(12) United States Patent
Rao et al.

(10) Patent No.: US 12,090,298 B2
(45) Date of Patent: Sep. 17, 2024

(54) ANTIMICROBIAL COATING EXTENDING PERFORMANCE OF NEEDLELESS CONNECTOR

(71) Applicant: CareFusion 303, Inc., San Diego, CA (US)

(72) Inventors: Archana Nagaraja Rao, San Diego, CA (US); Siddarth K. Shevgoor, San Diego, CA (US); George Mansour, San Diego, CA (US); Todd Oda, San Diego, CA (US); Ali Saleh, San Diego, CA (US); Tomas Frausto, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 677 days.

(21) Appl. No.: 16/785,372

(22) Filed: Feb. 7, 2020

(65) Prior Publication Data
US 2021/0244934 A1  Aug. 12, 2021

(51) Int. Cl.
*A61M 39/26* (2006.01)
*A61K 31/155* (2006.01)
*A61L 29/08* (2006.01)
*A61L 29/16* (2006.01)
*A61M 39/10* (2006.01)

(52) U.S. Cl.
CPC ........... *A61M 39/26* (2013.01); *A61K 31/155* (2013.01); *A61L 29/085* (2013.01); *A61L 29/16* (2013.01); *A61M 39/10* (2013.01); *A61L 2300/206* (2013.01); *A61L 2300/404* (2013.01); *A61M 2205/0205* (2013.01)

(58) Field of Classification Search
None
See application file for complete search history.

(56) References Cited

U.S. PATENT DOCUMENTS

| | | | |
|---|---|---|---|
| 5,707,366 A | 1/1998 | Solomon et al. | |
| 8,426,348 B2 | 4/2013 | Ou-Yang | |
| 8,512,294 B2 | 8/2013 | Ou-Yang et al. | |
| 8,574,660 B2 | 11/2013 | Weaver et al. | |
| 8,821,862 B2 | 9/2014 | Madhyastha et al. | |
| 9,149,624 B2 | 10/2015 | Lewis | |
| 9,216,440 B2 | 12/2015 | Ma et al. | |
| 9,399,125 B2 | 7/2016 | Burkholz | |
| 9,695,323 B2 | 7/2017 | Lin et al. | |
| 9,981,069 B2 | 5/2018 | Modak et al. | |
| 10,149,971 B2 | 12/2018 | Liu et al. | |
| 10,220,419 B2 | 3/2019 | Ryan et al. | |
| 10,376,686 B2 | 8/2019 | Burkholz et al. | |
| 10,391,295 B2 | 8/2019 | Ryan et al. | |
| 2009/0324738 A1 | 12/2009 | Krongauz | |
| 2010/0135949 A1 | 6/2010 | Ou-Yang | |
| 2015/0231309 A1 | 8/2015 | Bihlmaier et al. | |
| 2016/0287758 A1 | 10/2016 | Thiagarajan et al. | |
| 2017/0042636 A1 | 2/2017 | Young | |
| 2017/0120028 A1 | 5/2017 | Burkholz et al. | |
| 2017/0281824 A1 | 10/2017 | Ryan | |
| 2018/0250504 A1 | 9/2018 | Schultz | |
| 2019/0134151 A1 | 5/2019 | Bond et al. | |
| 2019/0160275 A1 | 5/2019 | Funk et al. | |
| 2019/0175794 A1 | 6/2019 | Meng et al. | |
| 2019/0217077 A1 | 7/2019 | Chambers | |
| 2019/0232039 A1 | 8/2019 | Erekovcanski et al. | |
| 2019/0234540 A1 | 8/2019 | Marici et al. | |
| 2019/0282795 A1 | 9/2019 | Fangrow | |
| 2019/0308006 A1 | 10/2019 | Erekovcanski et al. | |
| 2019/0344064 A1 | 11/2019 | Buchanan | |

FOREIGN PATENT DOCUMENTS

| | | | | |
|---|---|---|---|---|
| CA | 2745158 | | 6/2010 | |
| CA | 3057863 A1 | * | 10/2018 | ......... A61L 33/0005 |
| JP | 2003205158 | * | 2/2003 | |
| JP | 2003505158 | * | 2/2003 | |
| JP | 2018510003 | * | 4/2018 | |
| WO | WO-0107102 A2 | | 2/2001 | |
| WO | WO-2008014447 A2 | | 1/2008 | |
| WO | 2019178560 | | 9/2019 | |
| WO | 2018204206 | | 11/2019 | |

OTHER PUBLICATIONS

Written Opinion of the International Preliminary Examining Authority for Application No. PCT/US2021/016665, dated Jan. 24, 2022, 8 pages.
International Preliminary Report on Patentability from the International Preliminary Examining Authority for Application No. PCT/US2021/016665, dated Apr. 25, 2022, 12 pages.
International Search Report and Written Opinion for Application No. PCT/US2021/016665, dated May 19, 2021, 12 pages.

* cited by examiner

*Primary Examiner* — Melissa S Mercier
(74) *Attorney, Agent, or Firm* — Morgan, Lewis & Bockius LLP

(57) ABSTRACT

A needleless access connector having an access port and a sustained release antimicrobial coating only on a top surface of the access port is disclosed. The top surface of the access port can be defined by a top surface of a proximal end of a housing and a top surface of a head portion of a compressible valve disposed within an internal cavity of the housing. In certain embodiments of the present disclosure, the sustained release antimicrobial coating is on: (i) the top surface the proximal end of the housing, or (ii) the top surface of the head portion of the compressible valve, or (iii) the sustained release antimicrobial coating is only on both the top surface the proximal end of the housing and the top surface of the head portion of the compressible valve.

6 Claims, 3 Drawing Sheets

ANTIMICROBIAL COATING EXTENDING PERFORMANCE OF NEEDLELESS CONNECTOR

TECHNICAL FIELD

The present disclosure generally relates to needleless connectors, and, in particular, to needleless connectors having a sustained release antimicrobial coating to extend the performance life of such connectors.

BACKGROUND

Needleless access connectors (NAC) are widely used throughout the medical industry to connect and disconnect sources of medical fluid (e.g., a saline solution or a liquid medication) intended to be infused to a patient. Such connectors are commonly used with intravenous (IV) catheters connected through an arrangement of flexible tubing and fittings, commonly referred to as an "IV set", to a source of fluid, for example, an IV bag.

Bacteria and other microorganisms may gain entry into a patient's vascular system from access hubs and ports/valves upon connection to the NAC. Each access hub (or port/valve or connection) is associated with some risk of transmitting a catheter related bloodstream infection (CRBSI), which can be costly and potentially lethal.

To decrease catheter-related bloodstream infection (CRBSI) cases and to ensure connectors are used and maintained correctly, standards of practice have been developed, which include disinfecting and cleaning procedures. For example, the 2016 Infusion Nurses Standards (INS) guidelines recommend that needleless connectors should be consistently and thoroughly disinfected using alcohol, tincture of iodine or chlorhexidine gluconate/alcohol combination prior to each access.

The disinfection of the needleless connector is ultimately intended to aid in the reduction of bacteria that could be living on the surface and possibly lead to a variety of catheter related complications including the CRBSI events described before. Nurses will typically utilize a 70% IPA alcohol pad to complete this disinfection task by doing what is known as "scrubbing the hub." However, compliance to this practice and its efficacy do not appear rigorous. In addition, health care professionals tend to change NAC connectors often, e.g., at least weekly, to reduce infection due to potential build-up of bacteria. However, a continuing need exists to reduce potential bacterial infection and to extend the service life of needleless access connectors.

SUMMARY

Aspects of the subject technology relate to needleless access connectors with antimicrobial coatings thereon and in particular to needleless access connectors having access ports with sustained release antimicrobial coatings on a top surface of the access port.

A needleless access connector can comprise an access port defined by a top surface of a proximal end of a housing and a top surface of a head portion of a compressible valve reciprocally disposed within an internal cavity of the housing. For example, needleless access connector can include a housing having a proximal end defining an access port of the housing, a distal end including a base defining an outlet port of the housing, and an inner surface defining an internal cavity extending between the access and outlet ports; a compressible valve disposed within the internal cavity and configured to contact at least a portion of the inner surface, the compressible valve comprising a head portion and a compressible body portion extending distally from the head portion. In certain aspects of the present disclosure, the top surface of the proximal end of the housing and/or a top surface of the head portion of the valve are coated with a sustained release antimicrobial coating and/or the sustained release antimicrobial coating is slightly below the top surface on the inner surface of the internal cavity of the housing. In other aspects of the present disclosure, the sustained release antimicrobial coating is only on the top surface the proximal end of the housing and/or only on the top surface of the head portion of the compressible valve and/or only slightly below the top surface on the inner surface of the internal cavity of the housing.

Embodiments include one or more of the following features individually or combined. For example, the top surface of the proximal end of the housing can include a chamfer and the sustained release antimicrobial coating can be deposited in the chamfer. In some embodiments, the housing can comprise a polycarbonate (PC), a polyurethane (PU), a polyvinyl chloride (PVC), a styrene-butadiene rubber (SBR), a polyacrylic or acrylate, or combinations thereof. In other embodiments, the top surface of the head portion of the compressible valve can comprise a silicone elastomer. In still further embodiments, the sustained release antimicrobial coating can include a biodegradeable polymer, a mesh forming polymer, a temperature/pH sensitive polymer or combinations thereof; and in other embodiments, the sustained release antimicrobial coating comprises a chlorhexidine salt as an antimicrobial agent.

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Aspects of the subject technology relate to needleless access connectors (NAC) having access ports with a sustained release antimicrobial coating on a top surface of the access port. The top surface of an access port of a NAC can be defined by: (i) a top surface of a proximal end of a housing and can extend into an inner surface of an internal cavity; and (ii) a top surface of a head portion of a compressible valve reciprocally disposed within an internal cavity of the housing. In certain embodiments of the present disclosure, the sustained release antimicrobial coating is on: (i) the top surface the proximal end of the housing and extended slightly below the access port, or (ii) the top surface of the head portion of the compressible valve, or (iii) the sustained release antimicrobial coating is only on both the top surface the proximal end of the housing and the top surface of the head portion of the compressible valve.

Coating only a top surface of an access port of an NAC advantageously reduces the amount of antibiotic available with flow of medical fluid through the connector and thus reduces the antibiotic load on a patient using an NAC having only a top surface with an antimicrobial coating. Reducing antibiotic load is particularly advantageous when more than one NAC is used to deliver fluids to a patient. In addition, coating the top surface of the access port of an NAC with a sustained release antimicrobial coating advantageously can extend the service life of the NAC thereby reducing the need for frequent replacements of the NAC over a given period of time.

Figure 1A:
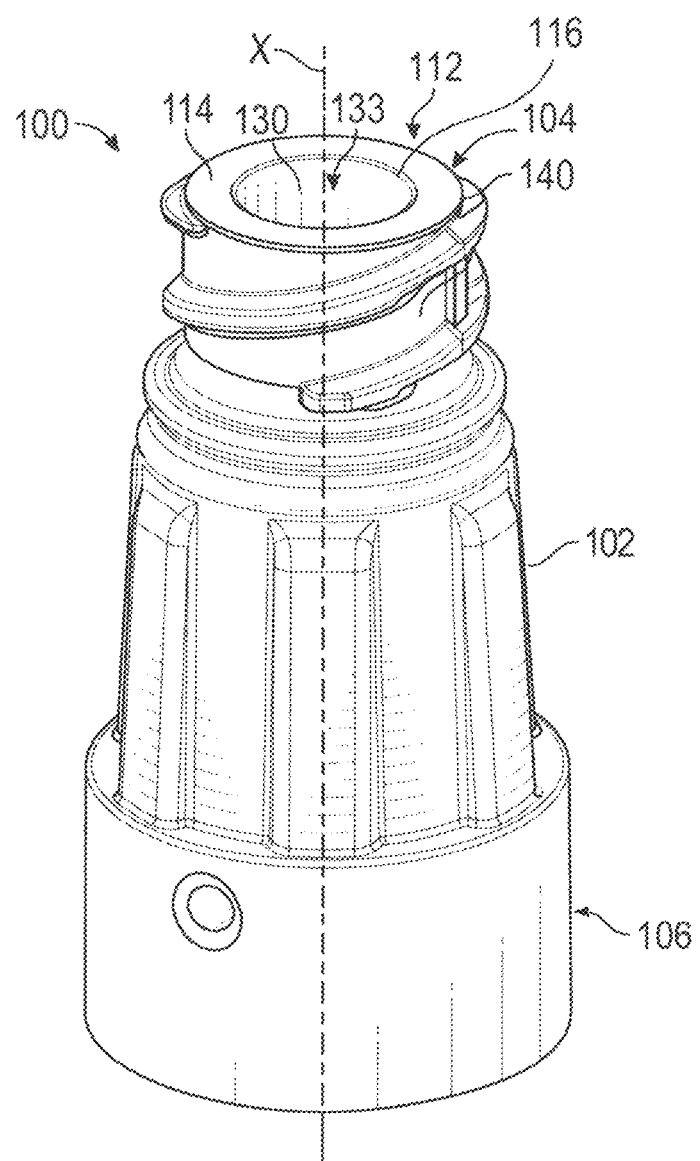
FIG. 1A illustrates a needleless access connector having an access port in accordance with some embodiments of the present disclosure.
Figure 1B:
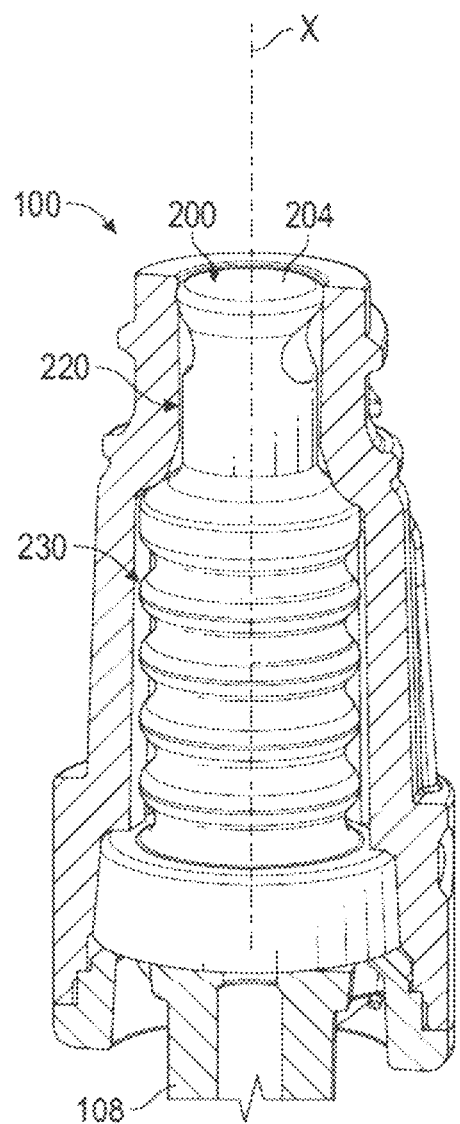
FIG. 1B illustrates a perspective view of the needleless access connector of FIG. 1A.

Referring to FIG. 1A, a perspective view of a needleless access connector having an access port is shown. FIG. 1B is a perspective view of a partial cutaway of the needleless access connector. As depicted in FIG. 1A and FIG. 1B, needleless access connector 100 includes housing 102 which has proximal end 104 and a distal end 106 defining outlet port 108 of housing 102. As referred to herein, proximally refers to an orientation toward top port surface 114 of the housing 102, and distally refers to an orientation toward the base portion 106 or bottom of the housing 102, opposite the top port surface 114.

Housing 102 includes an inner surface 130 defining an internal cavity 133 which extends at least partially between the proximal and distal ends 104 and 106, respectively. Needleless access connector 100 also includes compressible valve 200 disposed within internal cavity 133 of housing 102. Compressible valve 200 includes head portion 220 and compressible body portion 230 extending distally from the head portion 220. For this example, compressible valve is shown with a notched configuration in the head portion and ribbed configuration in the body portion but neither notches nor ribs are needed to practice the various aspects of the present disclosure.

Figure 2:
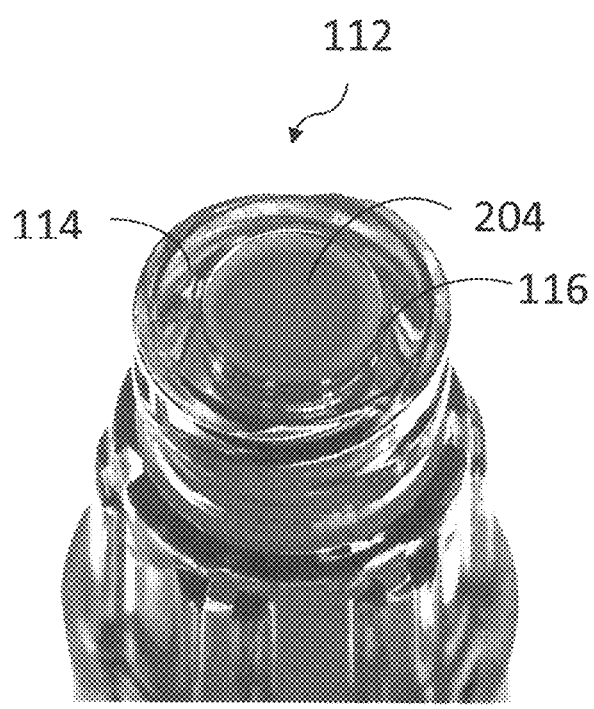
FIG. 2 illustrates an access port a needleless access connector in accordance with some embodiments of the present disclosure.

As further depicted in FIGS. 1A and 1B and also in FIG. 2, access port 112 is defined by top surface 114 of proximal end 104 of housing 102 and top surface 204 of head portion 220 of compressible valve 200. In certain embodiments, top surface 114 of proximal end 104 of housing 102 can include a chamfer 116 which contacts head portion 220 of compressible valve 200 when the valve is in a closed state. Top surface 114 of proximal end 104 of housing 102 and top surface 204 of head portion 220 of compressible valve 200 can include a certain amount of a sustained release antimicrobial coating. Applying an antimicrobial formulation to coat the chamfer or crevice on a top surface of an access port of an NAC can help control a predetermined volume of the coating on the top surface and thus a predetermined amount of the antimicrobial agent available at the access port. A predetermined depth of a chamfer or crevice helps to consistently apply an amount of antimicrobial coating to the access port in producing NAC and thus to have a consistent and predictable release rate in manufactured NACs.

Head portion of compressible valve forms a seal at or around top surface 114 of proximal end 104 of housing 102 thereby preventing ingress of materials. An additional advantage of including chamfer 116 with a sustained release antimicrobial coating at top surface 114 is to protect any potential vacant areas or areas not in sufficient contact between valve head 220 and inner surface 130 of internal cavity 133 when the valve is in the closed position. Should bacteria locate in such areas, the coating on the sustained release antimicrobial coating on the chamfer could eradicate such bacteria thus protecting the interface between the valve and the inner surface 130 of internal cavity 133 at and around the valve head In operation, compressible valve 200 of the needleless connector can compress and collapse when an axial force is applied to the top surface 204 of the compressible valve 200 and the valve can expand and realign when the axial force is removed. Hence, when an axial force (F) is applied to top surface 204 of the valve, the valve (200) compress within internal cavity 133 of housing 102 allowing a fluid path from access port 112 to outlet port 108.

Access port 112 can include engagement features 140 for coupling to another device (e.g., a fluid transfer assembly). For example, engagement features 140 may include cooperating mechanical elements, such as internal or external surface threads, detents, bayonet-type locking elements, etc., as well as other surface configurations, such as a tapered Luer surface for frictional engagement. In some embodiments, the inlet port 112 may define a female luer fitting with luer lock threading 140. In some embodiments, the outlet port 108 may include engagement features for coupling to another device or coupling to interconnect tubing. For example, the outlet port 108 may comprise a male luer-taper fitting and luer lock threading (not shown) for medical device implement interconnection. However, engagement features of the outlet port 108 may include other cooperating mechanical elements. In operation, a fluid pathway may be established through needleless connector from the access port 112 to the outlet port 108, for example.

An additional advantage of including a sustained release antimicrobial coating slightly below top surface 114 on inner surface 130 of internal cavity 133 is that such a coating can further protect ingress of active bacteria into the NAC. It is preferable that any antimicrobial coating on inner surface 130 of internal cavity 133 extend no further than the internal tapered luer section and preferably out of a fluid path when the NAC is connected with another implement. In certain aspects, a sustained release antimicrobial coating is no more than about 4 mm, such as less than about 3 mm, about 2 mm or about 1 mm below top surface 114 on inner surface 130 of internal cavity 133.

Housing 102, including top surface 114, can comprise one or more rigid polymeric materials such as a polycarbonate (PC), a polyurethane (PU), a polyvinyl chloride (PVC), a styrene-butadiene rubber (SBR), a polyacrylic or acrylate, or combinations thereof. Valve 200, including hear portion 220 and top surface 204, can comprise an elastic, inert material, such as a silicone elastomer, so that it is collapsible within the housing 102 and resists adversely interacting with medicinal fluids.

While current designs for NAC are robust to resist bacterial ingress, the access port is of particular concern since it is typically exposed to the environment when not connected to a medical implement. However, with a sustained release antimicrobial coating on a top surface of the access port, bacterial formation or build-up can be minimized or eliminated and these conditions can be maintained for one or more weeks of use. Hence in an aspect of the present disclosure, applying a sustained release antimicrobial coating onto only a top surface of an access port of a NAC.

Useful sustained release antimicrobial coatings on surfaces of access ports include those that are watersorable, flexible and durable. Such coatings can be formed from formulations that include one or more antimicrobial agents with one or more polymers. Alternatively, or in combination with one or more antimicrobial agents and polymers, the formulation can include polymer forming components, e.g. UV curable monomers and/or oligomers. The polymeric component of a formed antimicrobial coating are such that they can release the antimicrobial agent over time, e.g., over a period of at least 7 days, 14 days, 21 days, etc. The molecular weight of the polymer of the formed coating can be adjusted to control the release rate of the antimicrobial agent.

Useful polymers that can be included in formulations for preparing antimicrobial coatings of the present disclosure include, for example, biodegradeable polymers such as poly(lactic-co-glycolic acid) (PLGA), polycaprolactone (PCL), polyglycolide (PGL), polylactic acid (PLA), poly-3-hydroxybutyrate (PBH), polysaccharides, polyethylene glycol (PEG), polyethyleneoxide (PEO), mesh forming polymers such as cellulose acetate, temperature/pH sensitive polymers such as hyaluronic acid, poly(N-isopropylacrylamide) (NIPPam) etc. or co-polymers thereof and/or combinations thereof.

Useful polymer forming components that can be included in formulations for preparing sustained release antimicrobial coatings of the present disclosure include, for example, UV curable adhesives such as urethane acrylate curable adhesives or moisture or temperature curable adhesive components such as cyanoacrylates. UV curable formulation can include a combination of a urethane or a polyester-type oligomer with acrylate-type functional groups, acrylate-type monomers, as polymer forming components with an antimicrobial agent and optional photoinitiators, rheological modifiers, etc. Moisture or temperature curable adhesive components can include a combination of a cyanoacrylate and an antimicrobial agents, with optional activators, rheological modifiers, etc. The antimicrobial agents are preferably uniformly and distributed throughout the whole coating matrix A wide variety of UV curable oligomers can be used with formulations of the present disclosure. For example, the oligomers can be acrylated aliphatic urethanes, acrylated aromatic urethanes, acrylated polyesters, unsaturated polyesters, acrylated polyethers, acrylated acrylics, and the like, or combinations of the above. The acrylated functional group can be mono-functional, di-functional, tri-functional, tetra-functional, penta-functional, or hexa-functional.

As with the oligomers, a wide range of monomers can be used with formulations of the present disclosure Such monomers include, for example, 2-ethyl hexyl acrylate, isooctyl acrylate, isobornylacrylate, 1,6-hexanediol diacrylate, diethylene glycol diacrylate, triethylene glycol diacrylate, pentaerythritol tetra acrylate, penta erythritol tri acrylate, dimethoxy phenyl acetophenone hexyl methyl acrylate, 1,6 hexanidiol methacrylate, and the like, or combinations thereof.

To facilitate UV-curing, UV curable formulations can include an adequate and compatible photoinitiator. Such photoinitiators can be: 1) single molecule cleavage type, such as benzoin ethers, acetophenones, benzoyl oximes, and acyl phosphine oxide, and 2) hydrogen abstraction type, such as Michler's ketone, thioxanthone, anthroguionone, benzophenone, methyl diethanol amine, 2-N-butoxyethyl-4-(dimethylamino) benzoate, and the like, or combinations thereof. The UV curable formulation can be rapidly cured with ultraviolet light, e.g., curing can be completed in seconds or minutes depending on the formulation and curing conditions. The sustained release coatings of the present disclosure are generally efficacious within minutes.

Useful antimicrobial agents that can be included in formulations for preparing sustained release antimicrobial coatings of the present disclosure include, for example, aldehydes, anilides, biguanides, silver element or its compounds, bis-phenols, and quaternary ammonium compounds and the like or combinations thereof. In particular, suitable antimicrobial agents that can be included in formulations for preparing sustained release coatings of the present disclosure include, for example, a triclosan, a chlorhexidine salt such as chlorhexidine gluconate (CHG), chlorhexidine acetate (CHA), a chlorhexidine phosphanilate, a silver salt, a chlorhexidine/silver sulfadiazine. The antimicrobial agent can be included in a formulation the present disclosure in the amount of from about 0.5 to about 50 parts by weight in compared to 100 parts by weight of the formulation used to form the coating, e.g., in the amount of from about 0.5 to about 30 parts by weight of the formulation, such as from about 1 to about 20 parts by weight.

Some particular formulations that can be applied include, for example, a urethane acrylate adhesive with 8% CHA which can be applied to a top of a housing of an NAC followed by curing the formulation to form a sustained release antimicrobial coating thereon. A top surface of a valve for an NAC can be subjected to a primer, such as a primer for a silicone valve available from companies such as Henkel and Loctite, followed by applying a formulation including cyanoacrylate with 8% CHA and curing to form a sustained release antimicrobial coating on the valve. A silicone valve can be made more hydrophilic/wettable by plasma treatment or the valve can be etched so that an acrylate urethane adhesive formulation can be coated onto the top of the silicone valve.

Formulations for preparing sustained release coatings of the present disclosure can be prepared by mixing an antibacterial agent with a polymer, with or without solvent, to form a slurry or solution. Alternatively to mixing the antibacterial agent with a polymer, or in combination thereof, the antibacterial agent can be mixed with polymer forming components to prepare a formulation for preparing sustained release coatings. The formulation can then be applied to top surfaces by spray coating, dip coating, and/or wiping the formulation onto the surface. For example, a curable formulation for preparing a sustained release antimicrobial coating according to certain aspects of the present disclosure can be prepared by combining polymer forming components with about 8 wt % of an antimicrobial agent, e.g., fine powder of CHA (CHA can be ground to a small mesh/pore size so that it can mix to form an uniform distribution of the CHA in the formulation), to make a slurry. The slurry can then be applied to top surfaces.

As described above, an access port of an NAC includes a top surface of a compressible valve. Such valves are typically made from inert materials such as a silicone elastomer. However adhering a sustained release antimicrobial coating on such materials is challenging due to the relative inertness and flexibility needed for valves. To better adhere a sustained release antimicrobial coating on a top surface of a compressible valve, the surface can be modified.

Hence in an aspect of the present disclosure, prior to applying a sustained release antimicrobial coating on a surface of a valve, e.g., on a top surface of a silicone elastomeric valve, the surface of the valve is treated to made the surface more hydrophilic than an untreated surface. Such treatments can include, for example, treating with an alcohol such as isopropyl alcohol (IPA). The surface can also be made more hydrophilic by treating the surface of the valve with a plasma of oxygen, argon or both or by a pulse plasma wherein you can grow one or more desired monomer(s) on the surface sequentially to form a hydrophilic surface. The surface can be modified by applying a primer to the surface of the valve followed by applying an adhesive formulation. Such primers can be obtained from companies such as Henkel and Loctite.

Another way to facilitate adhere a sustained release antimicrobial coating on a top surface of a compressible valve it to modify the surface by creating a surface roughness for better adhesion. Further, the surface can be subjected to an ionized bombardment of the antimicrobial agent, e.g., CHA to modify the surface. The top surface of a valve can also be capped with a polymeric material having an antimicrobial agent to act as a sustained release antimicrobial coating on the surface of the valve.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless access connector comprising:
   a housing having a proximal end defining an access port of the housing, a distal end including a base defining an outlet port of the housing, and an inner surface defining an internal cavity extending between the access and outlet ports; and
   a compressible valve disposed within the internal cavity and configured to contact at least a portion of the inner surface, the compressible valve comprising a head portion and a compressible body portion extending distally from the head portion,
   wherein a top surface of the proximal end of the housing is coated with a sustained release antimicrobial coating,
   wherein a top surface of the head portion of the compressible valve is spaced from the top surface of the proximal end of the housing when the top surface of the head portion of the compressible valve contacts the housing in a closed state, and
   wherein the compressible valve is configured to collapse within the internal cavity upon application of axial force along an axis extending between the access port and the outlet port, thereby allowing a fluid path from the access port to the outlet port in an open state.

2. The needleless access connector of claim 1, wherein the top surface of the proximal end of the housing includes a chamfer and the sustained release antimicrobial coating is deposited in the chamfer.

3. The needleless access connector of claim 1, further comprising the sustained release antimicrobial coating slightly below the top surface on the inner surface of the internal cavity of the housing.

4. The needleless access connector of claim 3, wherein only the top surface on the inner surface of the housing is coated with the sustained release antimicrobial coating.

5. The needleless access connector of claim 1, wherein the sustained release antimicrobial coating comprises a chlorhexidine salt as an antimicrobial agent.

6. The needleless access connector of claim 1, wherein the sustained release antimicrobial coating releases the antimicrobial agent over a period of at least 14 days.

* * * * *